United States Patent
Loomis et al.

(10) Patent No.: US 6,534,560 B2
(45) Date of Patent: *Mar. 18, 2003

(54) BIORESORBABLE HYDROGEL COMPOSITIONS FOR IMPLANTABLE PROSTHESES

(75) Inventors: Gary L. Loomis, Morristown, NJ (US); D. Christian Lentz, Pompton Plains, NJ (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/957,427

(22) Filed: Sep. 20, 2001

(65) Prior Publication Data

US 2002/0035168 A1 Mar. 21, 2002

Related U.S. Application Data

(60) Continuation of application No. 09/395,725, filed on Sep. 14, 1999, now Pat. No. 6,316,522, which is a continuation-in-part of application No. 09/243,379, filed on Feb. 1, 1999, now Pat. No. 6,028,164, which is a continuation of application No. 09/145,588, filed on Sep. 2, 1998, now Pat. No. 6,005,020, which is a division of application No. 08/914,130, filed on Aug. 18, 1997, now Pat. No. 5,854,382.

(51) Int. Cl.$^7$ .................. A61L 27/00; A61L 29/00; A61L 31/00; A61F 3/12; A61F 6/00
(52) U.S. Cl. ............... 523/105; 523/111; 523/113; 623/8; 623/11.11; 424/401; 424/422; 424/423; 424/424; 424/426; 424/430; 424/433; 528/354; 528/361; 514/773.1; 514/772.2; 514/773; 514/777
(58) Field of Search .................. 523/105, 111, 523/113; 623/8, 11.11; 424/401, 422, 423, 424, 426, 430, 433; 528/354, 361; 514/772.1, 772.2, 773, 777

(56) References Cited

U.S. PATENT DOCUMENTS 6,316,522 B1 * 11/2001 Loomis et al. .............. 523/105

* cited by examiner

Primary Examiner—Nathan M. Nutter
(74) Attorney, Agent, or Firm—Hoffman & Baron, LLP

(57) ABSTRACT

Crosslinked compositions formed from water-insoluble copolymers are disclosed. These compositions are copolymers having a bioresorbable region, a hydrophilic region and at least two cross-linkable functional groups per polymer chain. Crosslinking of these polymers can be effected in solution in organic solvents or in solvent-free systems. If crosslinking occurs in a humid environment, a hydrogel will form. If crosslinking occurs in a non-humid environment, a xerogel will form which will form a hydrogel when exposed to a humid environment and the resulting crosslinked materials form hydrogels when exposed to humid environments. These hydrogels are useful as components in medical devices such as implantable prostheses. In addition, such hydrogels are useful as delivery vehicles for therapeutic agents and as scaffolding for tissue engineering applications.

13 Claims, No Drawings

BIORESORBABLE HYDROGEL COMPOSITIONS FOR IMPLANTABLE PROSTHESES

This application is a continuation of application of Ser. No. 09/395,725, filed on Sep. 14, 1999, now U.S. Pat. No. 6,316,522 which is a continuation-in-part of Ser. No. 09/243,379, filed on Feb. 1, 1999, now U.S. Pat. No. 6,028,164, which is a continuation of application Ser. No. 09/145,588, filed on Sep. 2, 1998, now U.S. Pat. No. 6,005,020 which is a divisional of Ser. No. 08/914,130, filed on Aug. 18, 1997, now U.S. Pat. No. 5,854,382.

FIELD OF INVENTION

This invention relates generally to compositions useful as components of medical devices. Particularly, the present invention relates to cross-linkable compositions formed from a water-insoluble copolymer having a bioresorbable region, a hydrophilic region and at least two cross-linkable functional groups per polymer chain. More particularly, this invention relates to such compositions comprising an organic solution. When crosslinked and exposed to a humid environment, these compositions form bioresorbable hydrogels. Furthermore, these compositions are useful as delivery vehicles for therapeutic agents. Processes for forming such hydrogels are also disclosed, as are processes for forming medical devices having such hydrogels incorporated therein.

BACKGROUND OF RELATED TECHNOLOGY

It is generally known to provide a porous material, such as an implantable prosthesis, with a biocompatible, biodegradable sealant or coating composition which initially renders the porous material substantially fluid-impermeable. Over time, such a sealant composition is resorbed and the healing process naturally takes over the sealing function as tissue ingrowth encapsulates the prosthesis. Naturally derived, as well as chemically synthesized, sealant compositions are well-known.

An example of a medical device having a sealing means is described at column 4, lines 38–55 of U.S. Pat. No. 5,843,160. Such sealing means preclude the egress of blood and prevent endoluminal leakage. A specific example of a sealing ring or sleeve is set forth at column 11, lines 10–36.

Natural materials, such as collagen and gelatin, have been widely used on textile grafts. U.S. Pat. Nos. 4,842,575 and 5,034,265 to Hoffman Jr., et al. disclose the use of collagen as a sealant composition for grafts. More recently, co-owned and co-pending U.S. Ser. No. 08/713,801 discloses the use of a hydrogel or sol-gel mixture of polysaccharides for rendering fluid-tight porous implantable devices. Such sealant compositions are beneficial in that they are able to seal an implantable device without the need for chemical modification of the surface thereof and provide improved bioresorbability as the healing process occurs. Furthermore, fibrin, an insoluble protein formed during the blood clotting process, has also been used as a sealant for porous implantable devices.

The use of such biologically-derived sealant compositions, however, suffers from several drawbacks. One such drawback is the difficulty in producing consistent coatings due to variations inherent in natural materials. Another drawback is that the body might identify such compositions as foreign and mount an immune response thereto. Thus, biologically-based sealant compositions can cause inflammation, as well as infection, at or around the site of implantation. This might lead to life-threatening complications.

Accordingly, attempts have been made to design sealant systems from chemically synthesized materials which are easy to manufacture, which are easy to control the desired characteristics and qualities thereof, and which have less potential for causing adverse biological reactions. For example, U.S. Pat. No. 4,826,945 to Cohn et al. discloses synthetically-produced resorbable block copolymers of poly (.alpha.-hydroxy-carboxylic acid)/poly(oxyalkylene) which are used to make absorbable sutures, wound and burn dressings, and partially or totally biodegradable vascular grafts. However, these copolymers are not crosslinked. The poly(alkylene) segments of such bio-absorbable copolymers are disclosed to be water-soluble so that the body can excrete the degraded block copolymer compositions. See also, Younes, H. and Cohn, D., *J Biomed. Mater. Res.* 21, 1301–1316 (1987) and Cohn, D. and Younes, H., *J Biomed. Mater. Res.* 22, 993–1009 (1988). As set forth above, these compositions are not crosslinked and, as a consequence, are relatively quickly bio-absorbed. Moreover, these non-crosslinked compositions generally require the presence of crystalline segments to retain their structural integrity. As a result of such crystalline segments, these compositions have limited utility as sealants for vascular grafts.

Furthermore, U.S. Pat. No. 4,438,253 to Casey et al. discloses tri-block copolymers produced from the transesterification of poly(glycolic acid) and a hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate, into the copolymer structure. The strength and flexibility which makes such a composition useful as a suture, however, does not necessarily make it appropriate for use as a sealant for a porous implantable prosthesis. Moreover, these tri-block copolymers are substantially non-crosslinked. Thus, while these compositions are somewhat hydrophilic, they do not form hydrogels.

Accordingly, attempts have been made to engineer biocompatible hydrogel compositions whose integrity can be controlled through crosslinking. For example, U.S. Pat. Nos. 5,410,016 and 5,529,914 to Hubbell et al. disclose water-soluble systems which, when crosslinked, utilize block copolymers having a water-soluble central block segment sandwiched between two hydrolytically labile extensions. Such copolymers are further end-capped with photopolymerizable acrylate functionalities. When crosslinked, these systems become hydrogels. The water-soluble central block of such copolymers can include poly(ethylene glycol), whereas the hydrolytically labile extensions can be a poly (.alpha.-hydroxy acid), such as polyglycolic acid or polylactic acid. See, Sawhney, A. S., Pathak, C. P., Hubbell, J. A., *Macromolecules* 1993, 26, 581–587. See also, U.S. Pat. No. 5,854,382, disclosing an aqueous emulsion of water-insoluble copolymer which is crosslinked to form a hydrogel.

Furthermore, U.S. Pat. No. 5,202,413 to Spinu discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as diisocyanate, diacylchloride, or dichlorosilane. The general structure of such a composition is R-(A-B-A-L).sub.x -A-B-A-R, where A is a polyhydroxy acid, such as polylactide, polyglycolide or a copolymer thereof, B is an oligomeric diol or diamine residue, L is a diacyl residue derived from an aromatic diacyl halide or diisocyanate, and R is H or an end-capping group, such as an acyl radical. A major difference between the compositions set forth in the Spinu '413 patent and those described by the Cohn references supra is that Spinu uses lactide blocks whereas Cohn uses lactic acid blocks. Furthermore, like the Cohn copolymers, the copolymers described in the Spinu '413 patent are not cross-linkable.

In general, all of the synthetic compositions set forth above describe copolymers having one or more segments which are water-soluble. Accordingly, many of the compositions described by these references are intended to be rapidly biodegraded by the body.

Thus, there is a need for water-insoluble, fully cross-linkable polymeric materials which are easily synthesized and provide controlled bioresorption in vivo. Moreover, there is a need for improved, cost-efficient, synthetic sealant compositions for porous, implantable prostheses which are characterized by their ability to self-emulsify and form stable, low viscosity emulsions. There is a further need for sealant compositions which are quickly cured, exist as hydrogels in an aqueous environment, and which remain flexible while dehydrated without the need for an external plasticizer. The present invention is directed to meeting these and other needs.

SUMMARY OF THE INVENTION

In one aspect of the present invention, there is provided a process for forming a covalently crosslinked composition in an organic solvent. This composition includes a water-insoluble copolymer which has a bioresorbable region, a hydrophilic region, and a plurality of cross-linkable functional groups per polymer chain. Use of an organic solution allows for a broader range of bioresorbable compositions to be used in the present invention than is possible where a substantially inorganic solvent alone is used. Individual uses for these compositions are as polymeric substrates, as scaffolding for tissue engineering, or as therapeutic agent delivery systems.

In another aspect of the present invention, there is provided a medical device which has, as at least one component thereof, a bioresorbable composition. This composition comprises a hydrogel formed from the crosslinking of a polymer containing a bioresorbable region, a hydrophilic region, a plurality of cross-linkable functional groups, and, optionally, a crosslinking agent, in an organic solution.

In a further aspect of the present invention, there is provided a process for forming a hydrogel. This process comprises providing a solution of a water-insoluble copolymer in an organic solvent. The water-insoluble copolymer includes a bioresorbable region, a hydrophilic region, a plurality of cross-linkable functional groups per polymer chain, and, optionally, a crosslinking agent. Crosslinking of the copolymer results in formation of a xerogel. This xerogel will form a hydrogel when exposed to a humid environment.

In a further aspect of the present invention there is provided another process for forming a hydrogel. This process comprises providing a solution of the above-mentioned water-insoluble copolymer in a solvent mixture comprised of a water-miscible organic solvent and water. Effecting a crosslinking reaction of the copolymer composition in this solution directly forms the hydrogel.

In yet a further aspect of the present invention, there is provided a process for forming a device, particularly a medical device, coated with a hydrogel. The hydrogel is formed from an organic solution which comprises a water-insoluble copolymer having a bioresorbable region, a hydrophilic region, a plurality of cross-linkable functional groups per polymer chain and, optionally, a crosslinking agent. This process comprises applying the solution to the medical device, initiating a crosslinking reaction, subsequently removing the organic solvent, and exposing the resulting xerogel to a humid environment to form a hydrogel.

DETAILED DESCRIPTION OF THE INVENTION

The present invention is directed to covalently crosslinked compositions formed from water-insoluble copolymers. The copolymers of the present invention include a bioresorbable region, a hydrophilic region, and a plurality of cross-linkable functional groups per polymer chain, and are present in an organic solution. Prior to being crosslinked, the water-insoluble copolymer compositions are soluble in organic solvents or solvent mixtures containing water-miscible organic solvents and water. Once crosslinked, such compositions form xerogels (dry gels) in the absence of water, or hydrogels in the presence of water. For purposes of the present invention, xerogels are crosslinked compositions which, when exposed to a humid environment, form hydrogels. Hydrogels (also known as aquagels) are materials that are able to swell rapidly in excess water and retail large volumes of water in their swollen structures. Hydrogels do not dissolve in water and maintain three-dimensional networks. They are usually made of hydrophilic polymer molecules which are crosslinked either by chemical bonds or by other cohesion forces such as ionic interaction, hydrogen bonding, or hydrophobic interaction. Hydrogels are elastic solids in the sense that there exists a remembered reference configuration to which the system returns even after being deformed for a very long time. (see Park et al, *Biodegradable Hydrogels for Drug Delivery*, Technomic Pub. Co., July 1993). These definitions are provided for reference only, and are not meant in any way to limit the materials to which these terms might apply. Xerogels or hydrogels formed from the compositions of the present invention can be introduced to a porous material to form a medical device.

Compositions of the present invention might also function as delivery vehicles for therapeutic agents. The use of organic solvents permits the rapid formation of various compositions containing water-insoluble additives and other water-insoluble polymers. The use of organic solvents makes it easier to incorporate certain pharmaceutical substances, as these substances are generally soluble in organic solvents. Additionally, organic solvents are easy to eliminate in the manufacturing process, simplifying the process of producing the compositions of the present invention, as well as the process of producing medical devices associated with hydrogels formed by the present invention. Further, organic solvents permit faster crosslinking of the polymer than will occur in the absence of organic solvents, and the use of organic solvents avoids the quenching of free radicals by water. Most additives, including other polymers, will be soluble in organic solvents, thereby facilitating their inclusion in compositions of the present invention.

The copolymers of the compositions of the present invention are multi-block copolymers including, for example, di-block copolymers, tri-block copolymers, star copolymers, and the like. For purposes of illustration only, a typical tri-block copolymer of the present invention may have the following general formula:

xABAx (I)

wherein A is the bioresorbable region, B is the hydrophilic region and x is the cross-linkable functional group. A specific example of a copolymer useful in the composition of the present invention has the following chemical structure:

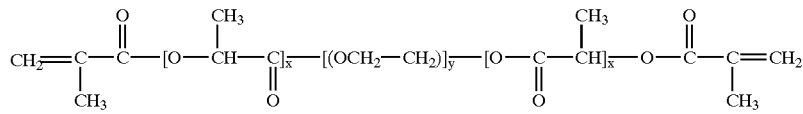

wherein x is from 10 to about 100 and y is from about 50 to about 500, so long as the composition remains substantially water-insoluble as a whole.

A more specific example of a copolymer useful in the composition of the present invention has the following chemical structure:

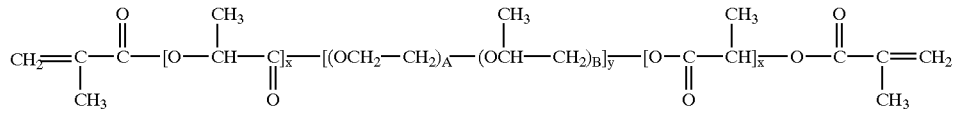

wherein the ratio of A to B is about 3:1, x is from about 10 to about 100, and y is from about 50 to about 300, so long as the composition remains substantially water-insoluble as a whole. wherein the ratio of A to B is about 3:1, x is from about 10 to about 100, and y is from about 50 to about 300, so long as the composition remains substantially water-insoluble as a whole.

One feature of the present invention is that the cross-linkable copolymer composition is substantially water-insoluble. For purposes of the present invention, "water-insoluble" is intended to mean that the copolymers of the present invention have water solubility in the range of about 0.0 gm/100 ml to about 0.5 gm/100 ml. A method for determining the water-solubility of copolymers of the present invention is set forth below in Example 5.

As set forth above, the water-insoluble copolymer of the composition of the present invention includes a bioresorbable region. For purposes of the present invention, the term "bioresorbable" means that this region is capable of being metabolized or broken down and resorbed and/or eliminated through normal excretory routes in the body. Such metabolites or break-down products should be substantially non-toxic to the body.

The bioresorbable region can be hydrophobic. In another aspect, the bioresorbable region can be designed to be hydrophilic so long as the copolymer composition as a whole remains substantially water-insoluble. The relative proportions or ratios of the bioresorbable to the hydrophilic regions, respectively, as well as any functional groups contained therein, are specifically selected to render the copolymer composition substantially water-insoluble. Furthermore, when crosslinked, these compositions are sufficiently hydrophilic to form hydrogels in aqueous environments. Such hydrogels, as set forth in more detail below, can form a fluid-impermeable barrier when applied to a porous material, particularly a medical device. The specific ratio of the two regions of the block copolymer composition of the present invention will, of course, vary depending upon the intended application and will be affected by the desired physical properties of the resulting hydrogels, the site of implantation, and other factors. For example, the composition of the present invention remains substantially water-insoluble when the ratio of the hydrophilic region to the hydrophobic region to is from about 5:1 to about 1:5, on a weight basis. Additionally, the selected ratios will depend on the relative hydrophilicity and molecular weights of the biodegradable and hydrophilic compounds chosen.

The bioresorbable region of the copolymer used in a composition of the present invention can be designed to be hydrolytically and/or enzymatically cleavable. For purposes of the present invention, "hydrolytically cleavable" refers to the susceptibility of the copolymer, particularly the bioresorbable region, to hydrolysis in water or in a water-containing environment. Similarly, "enzymatically cleavable", as used herein, refers to the susceptibility of the copolymer, particularly the bioresorbable region, to cleavage by endogenous or exogenous enzymes.

Based on the characteristics set forth above, a number of different compounds can comprise the bioresorbable region. The bioresorbable region can include, without limitation, for example, poly(esters), poly(hydroxy acids), poly(lactones), poly(amides), poly(ester-amides), poly(amino acids), poly(anhydrides), poly(ortho-esters), poly(carbonates), poly(phosphazines), poly(thioesters), polysaccharides and mixtures thereof. Furthermore, the bioresorbable region can also include, for example, a poly(hydroxy) acid including poly(.alpha.-hydroxy) acids and poly(.beta.-hydroxy) acids. Such poly(hydroxy) acids include, for example, polylactic acid, polyglycolic acid, polycaproic acid, polybutyric acid, polyvaleric acid, and copolymers and mixtures thereof.

The substantially water-insoluble copolymers of the present invention form solutions in organic solvents and in solvent mixtures containing water-miscible organic solvents and minor amounts of water. For the purposes of the present invention, an organic solution of the copolymer is defined as the copolymer in an organic solvent or the copolymer in a mixture of an organic solvent and up to about 50% water. Organic solvents which can be used, for example, are ethanol, 1-propanol, butanol, diethyl ether, dichloromethane, chloroform, dimethyl formamide, dimethyl acetamide, hexamethylphosphoramide, and toluene. These solvents are exemplary only and are not meant to be limit in any manner the solvents which may be used in the present invention. Another aspect of the present invention utilizes the copolymer in a liquid state without solvent.

As set forth above, the copolymer of the composition of the present invention also includes a hydrophilic region. For purposes of the present invention, "hydrophilic" is used in the traditional sense of a material or substance having an affinity for water. Although the copolymer contains a hydrophilic region, this region is designed and/or selected so that the copolymer composition, as a whole, remains substantially water-insoluble at all times.

When placed in vivo, the hydrophilic region can be processed into excretable and/or metabolizable fragments. Thus, the hydrophilic region can comprise, without limitation, for example, polyethers, polyalkylene oxides, poly(vinyl pyrrolidine), poly(vinyl alcohol), poly(alkyl oxazolines), polysaccharides, polypeptides, proteins, and copolymers and mixtures thereof. Furthermore, the hydrophilic region can also be, for example, a poly(alkylene) oxide. Such poly(alkylene) oxides can include, for example, poly(ethylene) oxide, poly(propylene) oxide, and mixtures and copolymers thereof;

As set forth above, the composition of the present invention also includes a plurality of cross-linkable functional groups. Any cross-linkable functional group can be included in the copolymer so long as the copolymer which includes the cross-linkable functional group is capable of forming a hydrogel. Cross-linkable functional groups which can be used in the present invention include olefinically unsaturated groups. Suitable olefinically unsaturated functional groups are, without limitation, for example, acrylates, methacrylates, butenoates, maleates, allyl ethers, allyl thioesters, and N-allyl carbamates.

The cross-linkable functional groups may be present at any point along the polymer chain of the present composition, so long as their location does not interfere with the intended function thereof, as set forth above. Furthermore, the cross-linkable functional groups may be present in the polymer chain of the present invention in numbers greater than two, so long as the intended function of the present composition is not compromised.

Preferably, at least two olefinically unsaturated functional groups are present on the polymer chain of the present composition. As set forth above, the number of olefinically unsaturated functional groups present on the polymer chain may be more than two, depending upon the particular application of the composition. Although the olefinically unsaturated functional groups may be positioned anywhere on the polymer chain of the present composition, it is preferred that at least one olefinically unsaturated functional group be positioned at a terminus of the polymer chain. More preferably, an olefinically unsaturated group is positioned at both terminal ends of the polymer chain. Furthermore, as there are at least two functional groups present in the copolymer composition, the functional groups contained therein may be the same or different.

Crosslinking of the polymer compositions of the present invention is accomplished through the cross-linkable functional groups. These functional groups can be activated by a variety of crosslinking means in order to crosslink the copolymer composition. These crosslinking means may include, for example, high energy radiation, thermal radiation, visible light, and combinations thereof. The composition of the present invention can also include free radical initiators. Such free radical initiators can include, for example, a peroxide or an azo compound. Preferably, a crosslinking agent used in the present invention is a free radical initiator, such as, for example, 2,2'-Azobis (N,N'dimethyleneisobutyrarnidine) dihydrochloride or benzoyl peroxide.

In the present invention, the composition is crosslinked in an organic medium, as set forth above. Furthermore, once crosslinked, the copolymer composition is able to form a hydrogel upon exposure to a humid environment. As set forth above, such hydrogels are polymeric materials that swell in water without dissolving and that retain a significant amount of water in their structures while maintaining dimensional stability. Such compositions have properties intermediate between those of liquids and solids. Hydrogels also deform elastically and recover, yet may flow at higher stresses. Hydrogel compositions of the present invention are less transient and can be controlled more easily than known non-crosslinked sealant compositions, as set forth previously. Thus, compositions of the present invention have distinct advantages over known compositions and have superior functionality as sealants for, as an example, porous materials, particularly implantable medical devices, and as delivery devices for, as an example, therapeutic agents.

In one aspect of the invention, a therapeutic agent, such as, for example, a drug or bio-active agent, can be introduced into the copolymer composition of the present invention. The drug or bio-active agent will be released in a controlled manner as the composition is bioresorbed. Thus, compositions of the present invention can be used to deliver therapeutic agents to specific sites in the body. Furthermore, such compositions can be engineered to bioresorb at particular rates by selecting the ratios of the bioresorbable regions to the hydrophilic regions as well as by controlling the degree of crosslinking and the molecular weight thereof. Thus, the present compositions are able to deliver controlled quantities of a therapeutic agent to a specific site in the body as the hydrogel is bioresorbed.

Any drug or bio-active agent can be incorporated into a composition of the present invention provided that it does not interfere with the required characteristics and functions of the composition. Examples of suitable drugs or bio-active agents include, for example, without limitation, thromboresistant agents, antibiotic agents, anti-tumor agents, antiviral agents, anti-angiogenic agents, angiogenic agents, anti-inflammatory agents, cell cycle regulating agents, their homologs, derivatives, fragments, pharmaceutical salts and combinations thereof.

Useful thrombo-resistant agents can include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antibiotics can include, for example, penicillins, cephalosporins, vancomycins, aminoglycosides, quinolones, polymyxins, erythromycins, tetracyclines, chloramphenicols, clindamycins, lincomycins, sulfonamides, their homologs, analogs, fragments, derivatives, pharmaceutical salts and mixtures thereof.

Useful anti-tumor agents can include, for example, paclitaxel, docetaxel, alkylating agents including mechiorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

Useful anti-viral agents can include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof.

In another aspect of the present invention, there is provided a medical device having associated with at least one surface thereof a bioresorbable coating composition of the present invention. This coating composition includes a hydrogel which is formed from the crosslinking of a polymer containing a bioresorbable region, a hydrophilic region, a plurality of crosslinked functional groups, and, optionally, a crosslinking agent, as set forth previously.

In particular, the present bioresorbable coating compositions are intended to coat medical devices made from implantable materials. These bioresorbable coatings are capable of rendering porous medical devices, such as conduits, vascular grafts, textile materials, polymeric films, and the like, substantially impermeable to fluid. For purposes of the present invention, "substantially impermeable to fluid" refers to the specific porosity of a material, such as a porous vascular or endovascular graft. Porosity of textile materials is often measured with a Wesolowski Porosity tester. With this apparatus, a graft is tied off at one end and the free end is attached to a valve on a porometer so that the graft hangs freely in a vertical position. Then, water is run through the graft for one minute and the water that escapes from the graft is collected and measured. The specific porosity of the graft is then calculated according to the following formula:

$$P = \frac{V}{A}$$

where V is the volume of water collected in ml/min and A is the surface area of the graft exposed to water in $cm^2$. A specific porosity of $\leq 1.0$ $ml/min/cm^2$ is considered an acceptable amount of leakage for an implantable vascular graft. Accordingly, for purposes of this invention, a substantially fluid-impermeable graft is defined as a graft with a specific porosity, after impregnation with a sealant of the present invention, of $\leq 1.0$ $ml/min/cm^2$. Porosities meeting and exceeding the acceptable specific porosity criteria set forth above can be achieved through the use of certain block copolymers described herein having polyether-polyester segments.

Implantable materials which can be used in the present invention can include, for example, polymeric materials, non-polymeric materials, and combinations thereof. The polymeric materials can include, for example, olefin polymers, including polyethylene, polypropylene, polyvinyl chloride, polytetrafluoroethylene, fluorinated ethylene propylene copolymer, polyvinyl acetate, polystyrene, poly (ethylene terephthalate), polyurethane, polyurea, silicone rubbers, polyamides, polycarbonates, polyaldehydes, natural rubbers, polyester copolymers, styrene-butadiene copolymers and combinations thereof. Non-polymeric implantable materials can include, for example, ceramics, metals, inorganic glasses, pyrolytic carbon and combinations thereof. The implantable materials set forth above are intended to be exemplary only and should not be construed in any way to limit the types of materials which may be used in the present invention.

As set forth above, the implantable materials may be used in the present invention can be used to manufacture medical devices, such as for example, endoprostheses. Grafts, stents and combination graft-stent devices are contemplated. Preferably, these medical devices are vascular or endovascular grafts. Useful vascular or endovascular grafts include those which are knitted, braided or woven, and can have velour or double velour surfaces. Alternatively, the medical device can be manufactured from an extruded polymer, such as polytetrafluoroethylene (PTFE), particularly expanded polytetrafluoroethylene (ePTFE), polyethylene terephthalate (PET), fluorinated ethylene propylene copolymer (FEP), polyurethane, silicone and the like. Composite structures are also contemplated.

In another preferred aspect, a medical device of the present invention can be a catheter, a guidewire, a trocar, an introducer sheath, or the like. When coated onto such devices, the composition of the present invention imparts increased bio-compatibility to one or more surfaces thereof. Furthermore, when the composition of the present invention includes a drug or bio-active agent, specific therapeutic effects can be imparted to the surfaces of such devices. Moreover, the hydrophilic region of the polymer composition of the present invention can impart increased lubriciousness to the surfaces of, for example, a guidewire or other similar device.

Thus, any medical device to which the bioresorbable coating composition of the present invention can adhere may be used for purposes of the present invention. Accordingly, the examples of implantable materials and medical devices set forth above are for purposes of illustration only and are not intended to limit the scope of the materials and devices to which the present bioresorbable coatings can be applied or otherwise associated therewith.

In another aspect of the present invention, pre-crosslinked and post-crosslinked polymers of the present invention can be used in tissue engineering applications as supports for cells. Appropriate tissue scaffolding structures are known in the art, such as the prosthetic articular cartilage described in U.S. Pat. No. 5,306,311, the porous biodegradable scaffolding described in WO 94/25079, and the prevascularized implants described in WO 93/08850 (all hereby incorporated by reference herein). Methods of seeding and/or culturing cells in tissue scaffoldings are also known in the art, such as those methods disclosed in EPO 422 209 B1, WO 88/03785, WO 90/12604, and WO 95/33821 (all hereby incorporated by reference herein). Additionally, the cross-linkable pre-polymers of the present invention can be used to encapsulate cells for tissue engineering purposes.

In another aspect of the present invention, there is provided a process for forming a hydrogel. This process includes: (1) providing an organic solution of a water-insoluble copolymer which contains a bioresorbable region, a hydrophilic region, a plurality of cross-linkable functional groups per polymer chain, and, optionally, a crosslinking agent, and (2) effecting a crosslinking reaction, as set forth previously, and (3) exposing the composition to a humid environment to form a hydrogel, where steps (2) and (3) do not have to be carried out in any particular order. In this process, the cross-linkable functional groups can be, but are not limited to, olefinically unsaturated groups. As set forth previously, the crosslinking agent can be a free radical initiator, such as an azo or a peroxide compound. Still further, the crosslinking reaction can be, for example, thermally or photochemically affected. The hydrogel is formed when the copolymer composition is exposed to a humid environment.

In yet another aspect of the present invention, there is provided a process for forming a medical device coated with a hydrogel. The hydrogel may be formed by a process as set forth above. The polymer composition may be introduced into the medical device and subsequently crosslinked. Alternatively, the polymer composition may be crosslinked prior to being introduced into the medical device. Once crosslinked, the polymer composition may form a hydrogel when exposed to a humid environment.

The crosslinking agent can be activated in both humid and non-humid environments. In some instances, it is preferred that the activation take place in a humid environment. In these cases, the hydrogel is formed directly. Preferably, the humid environment contains from about 20% to about 100% water. More preferably, the humid environment contains from about 60% to about 100% water. In cases where the crosslinking is effected in non-humid environments, the hydrogel is formed upon subsequent exposure of the crosslinked copolymer to a humid environment.

The hydrogels formed by the above process can be packaged and stored in a variety of ways. For example, the hydrogel can be maintained in a hydrated state for an extended period of time. Alternatively, the hydrogel can be dehydrated and stored in an essentially desiccated state until use, since the hydration and dehydration of these crosslinked copolymers is completely reversible. Furthermore, plasticizers can be added to the dehydrated materials to provide materials with increased flexibility. Plasticizers useful in this application include, but are not limited to, glycerol, propylene glycol, and triethyl citrate.

Certain copolymer compositions of the present invention are liquids and can be crosslinked in the absence of any solvent. When this solvent-free process is employed, the hydrogel is formed upon subsequent exposure of the crosslinked copolymer to an aqueous environment.

The following examples are set forth to illustrate the copolymer compositions of the present invention. These examples are provided for the purpose of illustration only and are not intended to be limiting in any sense.

EXAMPLE 1

Synthesis of lac-[peo/ppo]-lac Copolymer
Preparation of (Polymer A) According to the Present Invention was Synthesized as Follows:

100.46 gm poly(ethylene-glycol)-co-poly(propylene glycol)-co-poly(ethylene glycol) (75 wt % ethylene glycol, Mn=12,000) was charged to a 500 ml 4-neck reaction flask equipped with a Dean-Stark water trap, a water-cooled condenser, a thermometer, and a gas inlet/outlet system which allowed for the controlled flow of nitrogen. While maintaining a nitrogen atmosphere, 230 ml of anhydrous toluene was added to the flask, the mixture was heated, and reflux was maintained for approximately 1 hour. During this period, any water present was collected in the Dean-Stark water separator (approximately 30 ml of the original toluene was also removed during this azeotropic water removal). The flask was allowed to cool to room temperature and 45.5 gm D,L-lactide was added to the flask along with 605 mg zinc lactate (monohydrate) catalyst. The reaction mixture was heated to reflux for 16, hours during which time an additional 30 ml of toluene and was removed via the Dean-Stark water separator. 4.00 gm of triethylamine was added to the reaction mixture at room temperature, and, after 5 minutes of stirring, 3.34 gm of acryloyl chloride was slowly added to the flask. The mixture was then stirred at room temperature for 5.0 hours. Approximately 110 mg of 4-methoxy phenol was added to the flask as a free-radical inhibitor. The solution was then transferred to large centrifuge bottles and solid by-products were removed via centrifugation at 5° C.@9000 rpm followed by decantation of the clear supernatant solution. This solution was then reduced in vacuuo on a rotary evaporator at 60° C.@<25 mm Hg until all traces of solvent and other volatile materials were removed. The polymer thus prepared and isolated was a water-insoluble, viscous liquid at room temperature.

EXAMPLE 2

Synthesis of lac-[peo/ppo]-lac Copolymer
Preparation of (Polymer B) According to the Present Invention was Synthesized as Follows:

100.46 gm poly(ethylene-glycol)-co-poly(propylene glycol)-co-poly(ethylene glycol) (75 wt % ethylene glycol, Mn=12,000) was charged to a 500 ml 4-neck reaction flask equipped with a Dean-Stark water trap, a water-cooled condenser, a thermometer, and a gas inlet/outlet system, which allowed for the controlled flow of nitrogen. While maintaining a nitrogen atmosphere, 230 ml of anhydrous toluene was added to the flask, the mixture was heated to reflux, and reflux was maintained for approximately I hour. During this period, any water present was collected in the Dean-Stark water separator (approximately 30 ml of the original toluene was also removed during this azeotropic water removal). The flask was allowed to cool to room temperature and 71.44 gm D,L-lactide was added to the flask along with 605 mg zinc lactate.(monohydrate) catalyst. The reaction mixture was heated to reflux for 16 hours, during which time an additional 30 ml of toluene and was removed via the Dean-Stark water separator. 4.00 gm of triethylamine was added to the reaction mixture at room temperature, and, after 5 minutes of stirring, 3.34 gm of acryloyl chloride was slowly added to the flask. The mixture was then stirred at room temperature for 5.0 hours. Approximately 110 mg of 4-methoxy phenol was added to the flask as a free-radical inhibitor. The solution was transferred to large centrifuge bottles and solid by-products were removed via centrifugation at 5° C.@9000 rpm followed by decantation of the clear supernatant solution. This solution was then reduced in vacuuo on a rotary evaporator at 60° C. @<25 mm Hg to remove all solvent and other volatile materials. The polymer thus prepared and isolated was a water-insoluble, viscous liquid at room temperature.

EXMPLE 3

Synthesis of lac-[peo/ppo]-lac Copolymer
Preparation of (Polymer C) According to the Present Invention was Synthesized as Follows:

96.65 gm poly(ethylene-glycol)-co-poly(propylene glycol)-co-poly(ethylene glycol) (75 wt % ethylene glycol, Mn=12,000) was charged to a 500 ml 4-neck reaction flask equipped with a Dean-Stark water trap, a water-cooled condenser, a thermometer, and a gas inlet/outlet system which allowed for the controlled flow of nitrogen. While maintaining a nitrogen atmosphere, 230 ml of anhydrous toluene was added to the flask, the mixture was heated to reflux, and reflux was maintained for approximately 1 hour. During this period, any water present was collected in the Dean-Stark water separator (approximately 30 ml of the original toluene was also removed during this azeotropic water removal). The flask was allowed to cool to room temperature and 54.71 gm D,L-lactide was added to the flask along with 605 mg zinc lactate (monohydrate) catalyst. The reaction mixture was heated to reflux for 16 hours, during which time an additional 30 ml of toluene and was removed via the Dean-Stark water separator. 4.00 gm of triethylamine was added to the reaction mixture at room temperature, and, after 5 minutes of stirring, 3.34 gm of acryloyl chloride was slowly added to the flask. The mixture was then stirred at room temperature for 5.0 hours. Approximately 110 mg of 4-methoxy phenol was added to the flask as a free-radical inhibitor. The solution was transferred to large centrifuge bottles and solid by-products were removed via centrifugation at 5° C.@9000 rpm followed by decantation of the clear supernatant solution. This solution was then reduced in vacuuo on a rotary evaporator at 60° C.@<25 mm Hg to remove all solvent and other volatile materials. The polymer thus prepared and isolated was a water-insoluble, viscous liquid at room temperature.

EXAMPLE 4

Crosslinking of the Above Polymers in an Organic Solvent or an Organic/aqueous Solvent System and Physical Characterization of the Resulting Materials Preparation and Testing of Crosslinked Polymer Systems.

Each of the solutions described below was transferred to a shallow Teflon™ mold (9.0 cm×9.0 cm×1.0 cm) and sparged with argon to remove oxygen from the solution. The filled molds were then sealed with glass cover plates and heated in an oven for the duration and temperatures described below.

Solution 1 (Composition D)

To a solution of 15 wt % polymer A (prepared in Example 1) in 75:25 1-propanol/water was added Vazo 044™ initiator (20 mg/1.00 gm polymer). Solution was cured in a mold as described above for 6 hours at 75° C.

Solution 2 (Composition E)

To a solution of 30 wt % polymer C (prepared in Example 3) in anhydrous 1-propanol was added benzoyl peroxide (60 mg/1.0 gm polymer). Solution was cured in a mold as described above for 4 hours at 60° C.

Solution 3 (Composition F)

To a solution of 15 wt % of Polymer C (prepared in Example 3) in 50:50 1-propanol/water was added 2,2'-Azobis (N,N'-dimethyeneisobutyramidine) dihydrochloride [Vazo-44™], (40 mg/100 gm polymer). Solution was cured in a mold as described above for 4 hours at 60° C.

The resulting crosslinked compositions D, E and F were de-molded, washed three times in deionized water and three times in 1-propanol, and dried in vacuuo to afford small sheets of crosslinked polymer compositions. The compositions D, E and F thus obtained were flexible at room temperature and exhibited good elastic recovery when deformed. When exposed to aqueous environments, the compositions D, E and F absorbed water rapidly to afford dimensionally stable hydrogels.

Dumbbell-shaped tensile test specimens (length=38 mm, width at center=5 mm, width at ends=16 mm) were die cut from the above composition and stress-strain properties were determined on an Instron™ tensile tester using a uniaxial pull with a cross-head speed of 8.0 in/min and a distance of 1.0 in between grips. Results of this testing is shown in Table 1.

TABLE 1

| Composition | Tensile Strength (lb/in²) | Elongation at Break (%) |
| --- | --- | --- |
| D | 242 | 1474 |
| E | 199 | 1270 |
| F | 270 | 1557 |

EXAMPLE 5

Procedure for Determination of Water-solubility of Polymers

In a large centrifuge bottle, 2.0±0.2 gm of polymer was dispersed in 200.0±5.0 ml of distilled water by manual agitation for 20 minutes followed by 5 minutes of agitation in an ultrasonic bath, all at room temperature. This dispersion was then centrifuged at 9,000 rpm for 30 minutes, resulting in a clean separation onto an upper polymer phase and a lower polymer phase. A 125 ml aliquot of this upper aqueous layer was carefully removed via aspiration so as not to disturb the lower polymer phase. This 125 ml aliquot was lyophilized to afford a small quantity of extracted material. The % water-solubility of the polymer was calculated as follows:

% solubility in water=(weight of extracted material/original weight of polymer)×100 or solubility (grams/100 ml)=(weight of extracted material in grams)×(100 ml/125 ml)

As measured according to this procedure, the polymers of the examples presented have water solubility in the range of 0.012 to 0.058 gm/ 100 ml.

The invention being thus described, it will be obvious that the same may be varied in many ways. Such variations are not to be regarded as a departure from the spirit and scope of the invention and all such modifications are intended to be included within the scope of the following claims.

What is claimed is:

1. A composition comprising an organic solution of a water-insoluble copolymer having (1) a bioresorbable region; (2) a hydrophilic region; and (3) a plurality of cross-linkable functional groups per polymer chain of the following general formula:

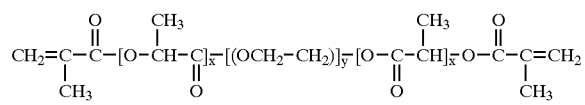

wherein x is from about 10 to about 100 and y is from about 50 to about 500, and a substantially non-aqueous organic solvent.

2. The composition of claim 1, wherein said water-insoluble copolymer has the following general formula:

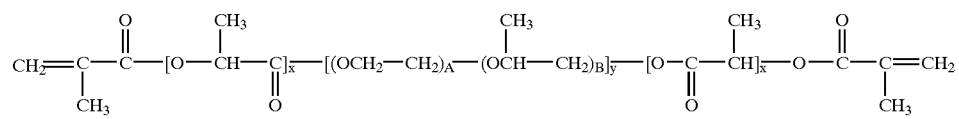

wherein the ratio of A to B is about 3:1, x is from about 10 to about 100, and y is from about 50 to about 300, so long as the composition remains substantially water-insoluble as a whole.

3. The composition of claim 1, wherein said water insoluble copolymer is selected from the group consisting of di-block copolymers, tri-block copolymers, and star copolymers.

4. The composition of claim 1, wherein said tri-block copolymer has the general formula:

xABAx wherein A is the bioresorbable region, B is the hydrophilic region, and x is the cross-linkable functional group.

5. The composition of claim 1, wherein said organic solution further comprises a mixture of an organic solvent and up to 50% water.

6. The composition of claim 1, wherein said solvent is selected from the group consisting of aliphatic and aromatic alcohols.

7. The composition of claim 1, wherein said bioresorbable region is selected from the group consisting of poly(esters), poly(hydroxy acids), poly(lactones), poly(amides), poly (ester-amides), poly(amino acids), poly(anhydrides), poly (ortho-esters), poly(carbonates), poly(phosphazines), poly (thioesters), polysaccharides and mixtures thereof.

8. The composition of claim 1, wherein said hydrophilic region is selected form the group consisting of polyethers, polyalkylene oxides, polyols, poly(vinylpyrrolidine), poly (vinyl alcohol), poly(alkyl oxazolines), polysaccharides, carbohydrates, peptides, proteins, and copolymers and mixtures thereof.

9. The composition of claim 1, wherein said bioresorbable region is hydrophilic.

10. The composition of claim 1, wherein said bioresorbable region has hydrophilic character without rendering the polymer water-soluble.

11. The composition of claim 1, wherein said hydrophilic region forms an excretable and/or metabolizable fragment.

12. The composition of claim 1, wherein said plurality of cross-linkable functional groups are olefinically unsaturated groups.

13. The composition of claim 1, wherein said composition further includes a free radical initiator.

* * * * *

UNITED STATES PATENT AND TRADEMARK OFFICE
CERTIFICATE OF CORRECTION

PATENT NO.    : 6,534,560 B2                                                Page 1 of 1
DATED         : March 18, 2003
INVENTOR(S)   : G. Loomis et al.

It is certified that error appears in the above-identified patent and that said Letters Patent is hereby corrected as shown below:

<u>Title page,</u>
Item [74], *Attorney, Agent, or Firm*, "Hoffman & Baron, LLP" should read
-- Hoffmann & Baron, LLP --.

<u>Column 8,</u>
Lines 47-48, "...including mechiorethamine..." should read -- including mechlorethamine... --.

<u>Column 13,</u>
Line 26, "...(40 mg/100 gm polymer)." should read -- (40 mg/1.00 gm polymer). --.

Signed and Sealed this

Eleventh Day of November, 2003

JAMES E. ROGAN
*Director of the United States Patent and Trademark Office*